United States Patent
Dodson et al.

(12)

(10) Patent No.: US 6,723,499 B2
(45) Date of Patent: Apr. 20, 2004

(54) METHOD FOR IDENTIFYING INHIBITORS OF DUAL SUBSTRATE ENZYMES

(75) Inventors: Heidi Sue Dodson, Novi, MI (US); James Scott Marks, Ann Arbor, MI (US); Thomas John McQuade, Ypsilanti, MI (US); Maxine Fico Santoro, Dexter, MI (US); Nicholas Santoro, Dexter, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/682,517

(22) Filed: Sep. 13, 2001

(65) Prior Publication Data

US 2003/0049705 A1 Mar. 13, 2003

(51) Int. Cl.⁷ .................................................. C12Q 1/00
(52) U.S. Cl. ............................................ 435/4; 435/15
(58) Field of Search ............................... 435/4, 15, 968

(56) References Cited

U.S. PATENT DOCUMENTS

2001/0031477 A1 * 10/2001 Reynolds et al. ............ 435/7.5

OTHER PUBLICATIONS

Gul, S., Sreedharan, S.K., and Brocklehurst, K., (1998) Enzyme Assays: Essential Data, pp. 37–44, John Wiley & Sons Ltd., Chichester, West Sussex, U.K.*

Mathews, C.K., van Holde, K.E., (1995) Biochemistry—Second Edition, p. 654, The Benjamin/Cummings Publishing Company, Inc., Menlo Park, CA, USA.*

He et al., "Development of a Scintillation Proximity Assay for β–Ketoacyl–acyl Carrier Protein Synthase III", *Analytical Biochemistry*, vol. 282, pp 107–114, 2000.

Verwoert et al., "Cloning, Nucleotide Sequence, and Expression of the *Escherichia coli* fabD Gene, Encoding Malonyl Coenzyme A–Acyl Carrier Protein Transacylase", *Journal of Bacteriology*, vol. 174, No. 9, pp 2851–2857, 1992.

Magnuson et al., "Cloning and nucleotide sequence of the fabD gene encoding malonyl coenzyme A–acyl carrier protein transacylase of *Escherichia coli*", *FEBS*, vol. 299, No. 3, pp 262–266, 1992.

* cited by examiner

*Primary Examiner*—Ralph Gitomer
(74) *Attorney, Agent, or Firm*—Cynthia Bott

(57) ABSTRACT

Methods are described for measuring the activity of dual substrate enzymes and for identifying compounds that inhibit such enzymes. The disclosed methods use a capture resin to bind to a first substrate of the dual substrate enzyme and a separation step to remove unreacted radiolabeled second substrate and the amount of radiolabeled first substrate is then measured by scintillation counting.

10 Claims, 3 Drawing Sheets

Figure 3. Results from performing the FabD assay with test compounds in a 96-well plate.
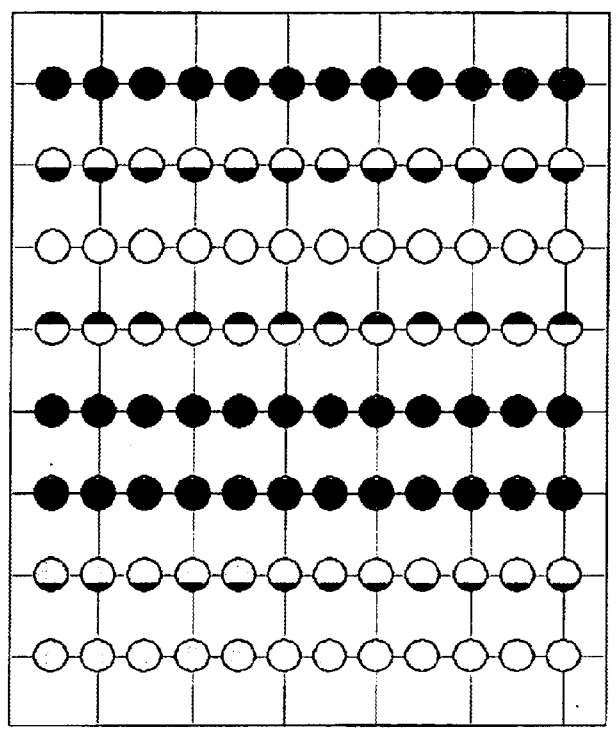

METHOD FOR IDENTIFYING INHIBITORS OF DUAL SUBSTRATE ENZYMES

FIELD OF THE INVENTION

This invention concerns a method for measuring the activity of dual substrate enzymes, and for identifying compounds that regulate such enzymes, and as such are useful for treating bacterial infections, disorders of lipid metabolism and cellular proliferation.

BACKGROUND OF THE INVENTION

Millions of individuals are afflicted with diseases that are caused by the inability to regulate important cellular processes such as fatty acid biosynthesis and cell proliferation. For example, the inability to regulate fatty acid biosynthesis results in lipid metabolism disorders that play a major role in diseases that include obesity, chronic hepatic encephalopathy, lipid diabetes, insulin resistant diabetes, and coronary heart disease. Failure to regulate cell cycle events can lead to unregulated cellular proliferation resulting in the growth of cancerous tissue and the malignant state. Some well known cancers that plague our society include breast cancer, prostate cancer and colon cancer. Thus, much research is carried out to understand fatty acid biosynthesis and cell proliferation to fulfill the need to treat these diseases and to maintain normal regulation of these processes. Much of the regulation of fatty acid biosynthesis and cell proliferation is carried out by enzymes. Often, too much or too little activity of specific enzymes can disrupt regulation of the processes they control. Since abnormal levels of activity of even a single enzyme can lead to the diseases described above, a great deal of research is being carried out to identify compounds that modulate the activity of key enzymes. For example, the enzyme acteyl CoA carboxylase (ACC) produces malonyl-CoA, which regulates fatty acid biosynthesis in cells. Mice lacking ACC were recently shown by Abu-Elheiga et al. (Science 291:2613–2616, 2001) to suffer major decreases in body fat (50%) despite increased food intake. Thus, inhibition of ACC might allow individuals suffering from obesity to lose weight while maintaining normal caloric intake.

Bacterial enzymes are also the focus of research to identify compounds that modulate enzyme activity, and thus can be used to treat bacterial infections. Resistance to commonly used antibiotics is widely prevalent and a growing concern in clinics and hospitals, thus causing a great demand today to identify new antibacterial compounds that are not plagued with resistance problems. Recently, much attention has been focused on targeting bacterial enzymes involved in fatty acid biosynthesis. In particular, enzymes involved in the bacterial fatty acid biosynthetic pathway are a popular target for the development of antibacterials for treating infectious diseases.

While some enzymes require a single substrate to function, others require two substrates. These are called dual substrate enzymes, or two-substrate enzymes. It is estimated that more than half of known biochemical reactions in mammals are catalyzed by dual substrate enzymes. Therapeutic areas whose drug discovery efforts focus on two-substrate enzymes include cancer, lipid metabolic disorders and anti-infectives. For example, some enzymes implicated in various cancers are kinases such as MEK, which are dual substrate enzymes. Enzymes involved in the fatty acid biosynthesis (FAB) pathway in the bacterial pathogen *E. coli* include malonyl coenzyme A-acyl carrier protein transacylase (FabD), B-ketoacyl-ACP reductase (FabG), B-ketoacyl-ACP synthase III (FabH) and enoyl-ACP reductase (FabI).

The current assays for identifying compounds that inhibit dual substrate enzymes have significant limitations. A new assay for the B-ketoacyl-ACP synthase III (FabH) was recently reported by He X. et al., 2000, Anal. Biochem. 282: 107–114. However, that assay is limited to using substrates that are radiolabeled with tritium, and substrates that are radiolabeled with other isotopes such as carbon-14 cannot be used in that assay. Assays for the identification of inhibitors of kinases often rely upon precipitation of a radiolabeled peptide or protein with trichloroacetic acid. Performing these assays requires the processing of large amounts of corrosive liquid, which is damaging to the instrumentation as well as the environment, and presents a high level of risk to the researcher. In addition, the use of viscous liquid scintillation cocktails in assays requiring radiometric detection presents a difficult challenge for high throughput screening processes. Individuals who perform these assays experience frequent equipment failure due to the corrosive liquid and precipitation of the peptide or protein. Consequently, these problems lower the quality of the assay, result in statistically unreliable data, and prohibit the use of these assays in high throughput screening processes. Furthermore, these conventional methods require numerous steps making the overall assay lengthy, and are an impediment to rapid drug discovery.

An object of this invention is to provide a rapid and reliable assay for identifying and analyzing compounds that modulate the activity of dual substrate enzymes.

SUMMARY OF INVENTION

This invention provides an assay for identifying and measuring the activity of compounds that interact with dual substrate enzymes. The assay utilizes a resin to capture and bind to one of the two substrates that interact with the dual substrate enzyme. Typical resins are in the form of beads, which can be charged. A typical substrate for the FabD enzyme is called Acyl Carrier Protein (ACP). The capture of ACP by a resin such as charged beads eliminates the need for trichloroacetic acid precipitation. The virtual unlimited surface area provided by such resins overcomes the limited binding capacity of standard microplate wells that are required by conventional assays. Use of these resins permits the use of a low-specific activity radiolabeled form of one of the substrates in the assay. Furthermore, the use of resins eliminates the need for modifying enzymatic substrates for capture, for example by synthesizing a biotinylated tag on the substrate. The present assay also uses scintillation proximity assay resins for measuring radioactivity, thus eliminating the need for liquid scintillation cocktails used in the prior art assays, which are comprised of toxic organic substances that are difficult to work with. The co-dispensing of resins (i.e., the capture resin and the scintillation resin) in this invention reduces the number of steps that must be performed according to prior art assays. The wide variety of commercially available resins that can be used in the present assay offers universal applications for substrate capture and scintillation counting. The utility of this invention is demonstrated by the measurement of enzyme activity and the activity of both known enzyme inhibitors, as well as potential inhibitors from chemical libraries.

This invention is a method for identifying an inhibitor of a dual substrate enzyme; wherein a first substrate is a macromolecule that is enzymatically modified in the presence of the dual substrate enzyme to accept the radiolabeled portion of a second substrate, said second substrate bearing a radiolabeled portion, such that some or all of the radiolabeled portion of the radiolabeled substrate is transferred to the macromolecule substrate to form a radiolabeled macromolecule, said method comprising:

a. adding a capture resin to a buffered mixture of an enzyme, a non-radiolabeled first substrate, a radiolabeled second substrate, allowing the enzyme to catalyze transfer of the radiolabeled portion of the radiolabeled second substrate to the non-radiolabeled first substrate, in the presence or absence of a test compound;

b. removing unreacted radiolabeled second substrate;

c. adding a scintillant resin to the enzyme-radiolabeled first substrate mixture; and d. measuring the amount of radiolabeled first substrate reacted in the presence of a test compound by scintillation counting, measuring the amount of radiolabeled first substrate reacted in the absence of a test compound by scintillation counting, and comparing the two measurements.

The assay provided by this invention includes a method wherein the first substrate is a macromolecule selected from a peptide or protein.

In a preferred embodiment, the first substrate is an Acyl Carrier Protein (ACP).

In another embodiment, the enzyme is selected from a fatty acid biosynthesis enzyme, a phosphate transfer enzyme, or a protein kinase enzyme.

Another embodiment of the invention includes use of a scintillation proximity assay resin (SPA) as the scintillant used for measuring the radiolabeled first substrate.

In a preferred embodiment of this invention, the unreacted radiolabeled second substrate is removed by filtration.

Another aspect of the invention is a method wherein the filtration of radiolabeled second substrate is carried out using an automated filtration and washing apparatus.

In another embodiment of the invention, the first substrate may be radiolabeled, with the second substrate being nonradiolabeled, and wherein the enzyme is an agent that catalyzes the transfer of the radiolabeled portion of said first substrate to said second substrate.

BRIEF DESCRIPTION OF DRAWINGS

FIG. 3 shows the results from performing FabD assays in individual wells of a 96-well microplate according to the method described in Example 1. The FabD reaction takes place in each well in the presence of a test compound from a chemical library. FabD activity measured in each well is compared to that of control wells (containing no test compounds) and is reported as percent inhibition. Levels of percent inhibition of FabD activity in each well is represented by shading. A black shaded dot represents a well with 50 to 100% reduction of FabD activity in the presence of a test compound. A gray shaded dot represents a well with 0–50% reduction in FabD activity in the presence of a test compound.

DETAILED DESCRIPTION

Figure 1A:
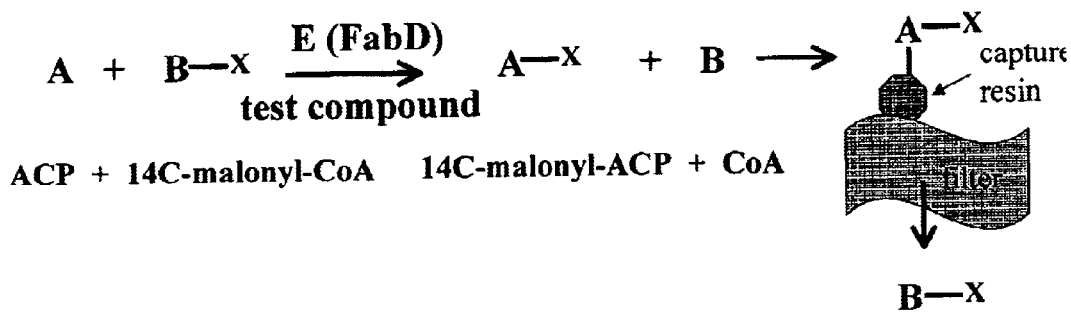
FIG. 1A shows a schematic representation of an enzyme (E), such as the malonyl coenzyme A-acyl carrier protein transacylase (FabD), catalyzing a transferase reaction involving two substrates. "A" means the non-radiolabeled first substrate, B means the radiolabeled second substrate, where "X" means the radiolabeled portion. In a typical example, the first substrate is acyl carrier protein (ACP), and the second substrate is malonyl-coenzyme A. The -X represents a radiolabeled malonyl group on the second substrate, the hexagon refers to the capture resin, and the flag represents a filter. In this reaction, the radiolabeled malonyl group of the second substrate, -X, is transferred from said second substrate to the non-radiolabeled first substrate, said transfer being affected by enzyme E.

The terms used in herein are defined as follows:

The term "macromolecule" means an organic molecule having a molecular weight of at least about 10,000 daltons and that participates in chemical reactions within the cells of mammals, bacteria and plants. Examples of classes of macromolecules include polysaccharides, proteins, lipids and nucleic acids. Specific examples of macromolecules include low density lipoproteins (LDL) hemoglobin, insulin, the acyl carrier protein, and fatty acid synthase.

The term "protein" means a macromolecule that is composed of a polymer of amino acids that are each covalently joined together through an amide linkage known as a peptide bond. A molecule referred to as a peptide generally means a protein having a molecular weight of less than 10,000 daltons, usually this means a polymer of less than 100 amino acids in length.

The term "dual substrate enzyme" means a compound that catalyzes a chemical reaction and requires a first substrate and a second substrate to function. The term is sometimes referred as "bisubstrate-enzyme" or "two-substrate enzyme". Most enzymes function within the cells of mammals, plants and bacteria. Alcohol dehydrogenase and trypsin are common enzymes and belong to a large group of enzymes known as transferases that catalyze the transfer of functional groups between two substrates. Families of transferases which are widely studied include the amino transferases and phosphotransferases such as kinases. A specific example of an amino transferase is glutamate-aspartate amino transferase. Specific examples of kinases are the mitogen-activated protein (MAP) kinases.

The term "Fab" means "fatty acid biosynthesis". Dual substrate enzymes that catalyze reactions in the fatty acid biosynthetic pathway are called "Fab" enzymes. Specific Fab enzymes include "FabD, which is an enzyme commonly found in *E. coli* cells and termed malonyl coenzyme A-acyl carrier protein transacylase. The term FabD as used herein includes all malonyl coenzyme A-acyl carrier protein transacylases with at least 30% protein sequence identity to the *E.* coli FabD. Examples include the FabD from Staphylococcusaureus (38% identity) and Streptococcuspneumoniae (45% identity), as well as the FabD from bacteria belonging to the genus Actinobacillus and Enterococcus. Other specific Fab enzymes include FabG, FabH and FabI. FabG is B-ketoacyl-ACP reductase. FabH is B-ketoacyl-ACP synthase III. FabI is enoyl-ACP reductase.

All of the Fab enzymes useful in the method of this invention are well known, and are either commercially available or readily prepared by methods well known to those skilled in the art of biochemistry. FabD, for example, is conveniently prepared by the method of Magnuson, K. et al., 1992, FEBS 299: 262–266; Verwoert, I. et al., J. Bacteriol., 174: 2851–2857.

"First substrate" as used herein means one of two compounds that are responsive to the catalytic effects of a dual substrate enzyme. "Second substrate" as used herein means a second compound responsive to the catalytic effects of said dual substrate enzyme. Another type of dual substrate enzymes are called "signal transduction enzymes". These include any dual substrate enzyme involved in signal transduction reactions within a cell. Signal transduction enzymes include, but are not limited to, phosphate transfer enzymes, such as kinases and phosphatases. Examples of specific kinases and phosphatases include the family of cyclin-dependent kinases (CDK), the mitogen-activated protein kinases (MAPK), the extracellular signal regulated kinases (ERK), and the tyrosine kinase encoded by the Wee1 gene.

The term "first substrate" means any macromolecule, such as a peptide or a protein. One example of a first substrate used in the present invention includes the acyl carrier protein (designated "A", FIG. 1A). Another example is a derivative of the acyl carrier protein that possesses a $^{14}$C-radiolabeled malonyl group (designated "A-x" FIG. 2A). Another example of a first substrate includes proteins or peptides that are substrates in kinase reactions (designated "A", FIG. 1B). Another first substrate envisioned by this invention includes phospho-peptides that are substrates in phosphatase reactions (designated "A-x", FIG. 2B).

Figure 1B:
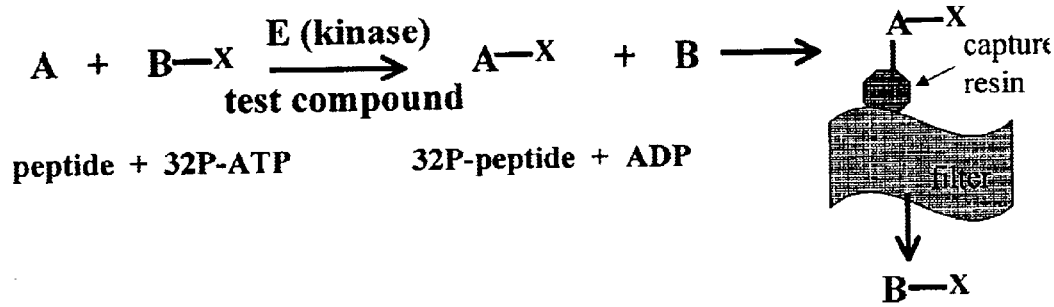
FIG. 1B shows a kinase enzyme catalyzing a transferase reaction involving two substrates. The first substrate is a protein or peptide, and the radiolabeled second substrate is adenosine triphosphate (ATP). The symbols are the same as in FIG. 1A except that the -X represents a radiolabeled phosphate group of said second substrate.
Figure 2A:
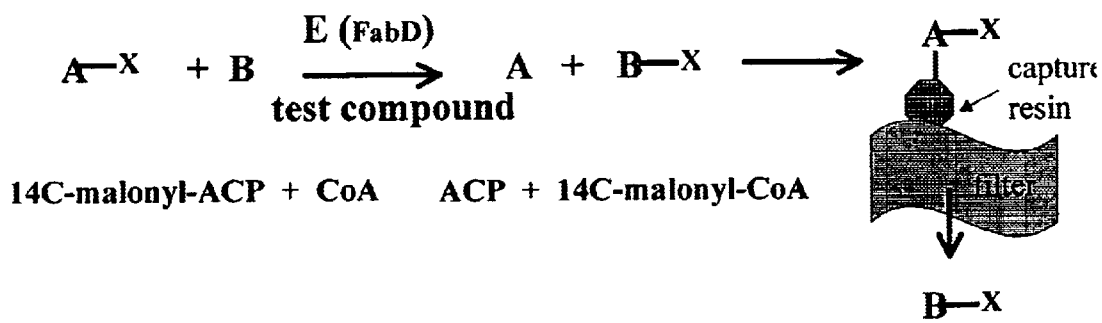
FIG. 2A shows a schematic of a transferase reaction catalyzed by the enzyme (E) malonyl coenzyme A-acyl carrier protein transacylase, FabD. This reaction is the reverse of that in FIG. 1A. Namely, the first substrate is radiolabeled malonyl-ACP, and the second substrate is non-radiolabeled coenzyme A. The -X means that the first substrate, malonyl-ACP, carries a radiolabeled malonyl group, otherwise the symbols are the same as in FIG. 1A.
Figure 2B:
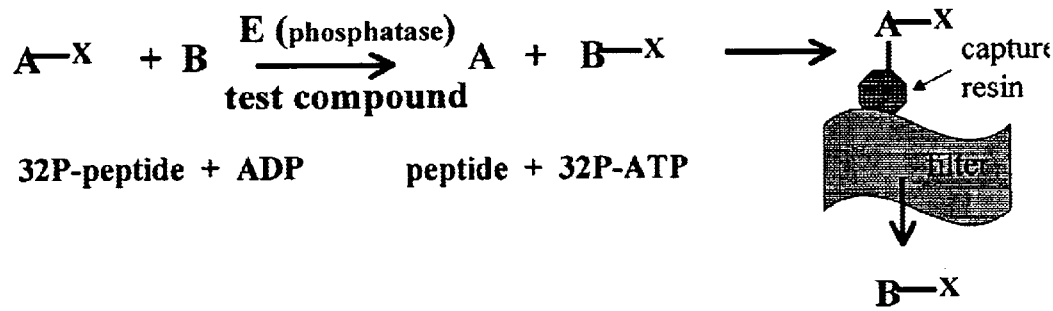
FIG. 2B shows a transferase reaction catalyzed by a phosphatase enzyme. The first substrate is a radiolabeled protein or peptide and is phosphorylated, the second substrate is adenosine diphosphate (ADP). The -X means that the first substrate is a peptide or protein possessing a radiolabeled phosphate group, otherwise the symbols are the same as in FIG. 2A.

The term "second substrate" means an organic molecule, such as, but not limited to, $^{14}$C-radiolabeled malonyl-CoA (designated "B-x", FIG. 1A). Another example of a second substrate includes coenzyme A (designated "B", FIG. 2A). Another example of second substrate envisioned by this invention includes adenine nucleotide bases such as, but not limited to, $^{32}$P-radiolabeled adenine nucleotide triphosphate also known as ATP (designated "B-x", FIG. 1B). Yet another example of a second substrate includes adenine nucleotide bases such as, but not limited to, $^{32}$P-radiolabeled adenine nucleotide diphosphate also known as ADP (designated "B", FIG. 2B).

The term "malonyl coenzyme A" or "malonyl CoA" means an organic compound that is a malonyl analog of naturally occurring coenzyme A.

The term "radiolabeled-substrate" means a first substrate or a second substrate that possesses a radiolabeled component capable of detection by scintillation counting. Any of the radioactive isotopes of common elements can be utilized to prepare radiolabeled substrates for use in the present method. Typical radioactive elements commonly employed include $^{14}$C, $^{3}$H, $^{125}$I, $^{32}$P, $^{33}$P, $^{35}$S, and the like. Radiolabeled substrates are generally available commercially, or can be prepared by synthetic methodologies well known to those skilled in the art. For example, a radiolabeled derivative of malonyl coenzyme A possessing a $^{14}$C moiety was obtained from PerkinElmer Life Sciences, Boston, Mass. Another example of a radiolabeled substrate is a peptide or protein possessing a phosphate group, e.g., a phospho-peptide or phospho-protein, where the non-radioactive phosphorous atom is replaced with the radionucleotide $^{32}$P by commercial methods.

The term "acyl carrier protein" or "ACP" means a protein substrate that is involved in fatty acid biosynthesis and whose role is to hold onto the growing fatty acid chain as it is being synthesized.

The term "buffer" means a compound or mixture of compounds that, when placed in an aqueous medium, resist changes in hydrogen ion concentrations when an acid or base is added.

The term "scintillant" means a compound that is stimulated by a radioactive molecule to emit light. The emitted light can be measured by conventional equipment.

The term "resin" as used herein is a solid support possessing functional chemical groups that can interact with and bind (i.e., capture) a macromolecule substrate. The term "ionically charged resin" means a resin that carries either a positive or negative charge, i. e. an anion or cation exchange resin, respectively. One example of an ionically charged resin is a "Source Q" resin purchased from Amersham Pharma Biotech (Piscataway, N.J.). Other ionically charged resins are commercially available and can be utilized in the method of this invention as the capture resin. Commonly used resins are in the form of monodispersed spherical beads made of synthetic polymers, such as Source Q, Source S, Mono Q and Mono S from Amersham Pharma Biotech (Piscataway, N.J.). Other commonly used resins available from Amersham Pharma Biotech (Piscataway, N.J.) are in the form of larger spherical beads and are made of cross-linked dextran, such as Sephadex, cross-linked agaroses, such as Sepharose, and cellulose, such as Sephacel.

The term "scintillation proximity assay bead" or "SPA bead" means a bead capable of absorbing energy from a radioactive substrate and thereby stimulated to emit light at a detectable wavelength for scintillation counting. The scintillation proximity assay bead used in the present invention can be purchased from Amersham Pharma Biotech (Piscataway, N.J.). SPA technology and SPA reagents are proprietary to Amersham Pharma Biotech (Piscataway, N.J.).

The term Flusher ™ means an automated filter washing device marketed by the PMS division of Digital Imagers, (Cathedral, Calif.).

EXAMPLE 1 (FIG. 3)

A METHOD FOR THE RAPID IDENTIFICATION OF COMPOUND THAT INHIBIT THE MALONYL COENZYME A-ACYL CARRIER PROTEIN TRANSACYLASE (FabD)

The materials used in the FabD assay are as follows:

FabD—glycerol stock of 10 μM, E. coli sequence with His tag added, purified by Pfizer Inc.;

$^{14}$C-malonyl-CoA 50 mCi/mmol, from PerkinElmer Life Sciences (Boston, Mass.);

Acyl Carrier Protein (ACP) Supplied by Sigma-Aldrich (St. Louis, Mo.) in 25 mg bottles;

Empigen BB 30%, a detergent from Calbiochem-Novabiochem (San Diego, Calif.) useful as a diluent for the buffer medium;

compound plate—a polypropylene surface having a multiplicity of compartments into which 1 μL of a 1 mM solution of a test compound in dimethyl sulfoxide (DMSO) is placed;

Source 15Q beads—from Amersham Pharmacia Biotech (Piscataway, N.J.) catalog #17-0945-01, 15 μm polystyrene, quartenary ammonium modified, supplied as 50% slurry;

TEA: triethanolamine 1 M buffer pH 7.7 prepared by mixing equal volumes of 1M Triethanolamine HCl acid (fw=185.7) and 1M Triethanolamine free base (fw=149.2);

SPA PVT—Glutathione beads from Amersham Pharmacia Biotech (Piscataway, N.J.) catalog #RPNQ 0030, 750 mg/bottle;

Filter plates—from Corning Inc., Life Sciences (Acton, Mass.), catalog #3504, 0.2 μm PVDF filter w/plastic bottom;

sodium chloride, 5M stock;

DTT: dithiothreitol;

EDTA—ethylenediaminetetraacetic acid, 0.5M stock, from Life Technologies (Rockville, Md.);

Multimek™ tips-200 μL Robbins autotips, colorless;

Multidrop cassettes, 3, accurate at 20 μL, 30 μL, and 200 μL, respectively;

barcode scanner;

disposable Robbins reservoirs.

Automated equipment used in this example:

Multimek™ with 96-tip head, from Beckman Coulter Inc. (Fullerton, Calif.);

Multidrop 384, from Titertek Instruments, Inc. (Huntsville, Ala.);

Trilux MicroBeta™ Counter, from PerkinElmer Life Sciences (Wallac) Inc., (Gaithersburg, Md.);

Flusher™ plate washer, from the PMS Division of Digital Imagers (Elburn, Ill.).

Methods

This assay measures the following enzymatic reaction of FabD:

Acyl Carrier Protein(ACP)+$^{14}$C Malonyl-CoA→$^{14}$C Malonyl-ACP+CoA

Acyl Carrier Protein(ACP) is highly anionic (22 acidic residues out of 77 total). This assay takes advantage of this property to separate the radiolabeled Mal-ACP product from the unreacted Mal-CoA remaining in the reaction. The present assay performs the enzymatic reaction in a polypropylene 96-well plate. At the end of the reaction, an aliquot is transferred to a filtration plate containing a mixture of cationic polystyrene and SPA scintillation beads. The cationic beads capture the ACP by electrostatic interaction. The beads are then filtered and washed to remove any unincorporated $^{14}$C Malonyl-CoA. The salt concentration of the wash buffer was optimized to bind Mal-ACP but elute Mal-CoA. The SPA scintillation beads permit the bound $^{14}$C Mal-ACP product to be quantitated in a microplate scintillation counter.

Source 15 Q beads were equilibrated as follows: Sixteen mL of Source 15 Q beads (50% slurry) were washed in 50 mL of Wash Buffer (20 mM TEA, pH 7.5 150 mM NaCl) and filtered to dryness (Corning 200 mL filter unit #25932, 0.2 micron filter). The beads were resuspended in 50 mL of 20 mM TEA, pH 7.5, 1M NaCl and filtered to dryness. Beads were again resuspended in 50 mL Wash Buffer and filtered to dryness. Finally, the Source 15 Q beads were resuspended in approximately 3.5 liters of Wash Buffer. Twenty seven bottles of SPA beads (750 mgs per bottle) were resuspended in 10 mL Wash Buffer and added to the equilibrated Source 15 Q beads. The final volume of the Source 15 Q/SPA bead solution was adjusted to 4 liters with Wash Buffer.

The assay solutions were prepared as follows:

1. Four 25 mg bottles of ACP were dissolved in a total of 600 mLs of reaction buffer (33 mM TEA, 84 mM NaCl, 2 mM EDTA, 0.3% Empigen BB, and 10 mM DTT). A 10 μM glycerol stock of FabD enzyme was diluted 1:500 in reaction buffer. Six hundred microliters of this diluted enzyme was added to the prior solution of ACP. This yielded a final concentration of 17 μM ACP and 20 pM FabD in reaction buffer.

2. Two bottles of $^{14}$C-malonyl-CoA (400 microcuries, 8 micromoles) were diluted in 500 mL purified water to a final concentration of 16 μM.

3. The Source 15 Q/SPA bead solution was stirred on a stir plate next to the Multidrop.

Ninety-six organic molecules (test compounds) were obtained from a chemical library and dissolved in DMSO to a concentration of 1 mM. Each of the solutions of test compounds were added to individual compartments of a polypropylene 96-well plate. To each compartment was then added 20 μL $^{14}$C malonyl-CoA (final concentration 6 μM) in reaction buffer. To each solution was added 30 μL of a solution of FabD and ACP in reaction buffer (final concentrations 12 pM and 10 μM, respectively). The reaction mixtures were allowed to stand for about 30 minutes at 24° C. 20 μL of each of the 96 reaction mixtures were transferred into a 96-well filter plate containing 200 μL of Source 15Q/SPA beads (capture and scintillation beads). The filter plate was stored at 24° C. for about 30 minutes to about four hours. The liquid portion from each compartment was withdrawn by vacuum filtration, and the semi-dry filter plate was washed one time with 200 μL of reaction buffer. The radioactivity of the mixture in each compartment was measured by scintillation counting using a Trilux MicroBeta™ Counter. Compartments exhibiting high radioactivity (approximately equal to that of control compartments containing no test compounds or enzyme inhibitors) contained test compounds that are inactive at inhibiting the FabD enzyme. Compartments exhibiting less radioactivity compared to the control compartment contain test compounds that were effective at inhibiting the catalytic effects of the FabD enzyme. The results of the foregoing assay are depicted in FIG. 3.

An example using the invention to assay 200 96-well plates:

1. _____ Remove compound plates, DTT, FabD, $^{14}$C-malonyl-CoA, and ACP from freezer. Remove lids from compound plates and thaw.

2. _____ Apply barcodes to 200 filter plates. Number the top and bottom plate of each stack with the stack number and place plates on the cart by Multidrop.

3. _____ Place thawed compound plates in stacks 15, then number the top plate of each stack w/the stack number. Place a control plate as the first plate in stack one, and as the bottom plate of stacks 2, 4, 6, 8, 10, 12, & 13.

4. _____ Clean multidrop cassettes: wipe exterior of tips with 70% ethanol. Clean tubing with 50 mL water, 15 mL ethanol, and 50 mL water.

5. _____ Load tips onto Multimek™, fill tip wash reservoir with 100 mL water and place on Multimek™ deck.

6. _____ Open Excel on barcode scanner computer. Make sure Autosave is ON (tools menu). Select "Save As" from file menu. Name file yymmddBA and save to "FabD barcodes" folder on desktop.

7. _____ Place carboy of Wash Buffer next to Flusher™ and place Flusher™ tubing into carboy.

8. _____ Check Flusher™ waste, empty if necessary.

9. _____ Turn on vacuum pump (push green button).

10. \_\_\_\_\_ Prime Flusher™. Black and white valve should be open (valve parallel with tubing=open). Choose "other" on Flusher™ screen (red button). Choose prime channel 1 (gray button w/return symbol. Repeat the prime step if necessary.

11. \_\_\_\_\_ Wet Flusher™ gasket with water using a squirt bottle.

12. \_\_\_\_\_ Prime Multidrop 1 with $^{14}$C-malonyl-CoA solution. Set Multidrop to deliver 20 µL.

13. \_\_\_\_\_ Prime Multidrop 2 with FabD/ACP solution. Set Multidrop to deliver 30 µL.

14. \_\_\_\_\_ Prime Multidrop 3 with bead solution and begin adding beads to filter plates, 200 µL/well. Start dispensing beads approximately 30 minutes prior to starting the reaction plates.

15. \_\_\_\_\_ Begin sequentially delivering C-malonyl-CoA and then FabD/ACP solution to compound plates every 30 seconds, when audibly prompted by timer. Mark time on numerous plates. Pause for 2 minutes after every 15$^{th}$ plate. Incubate each plate 30 minutes before transfer step. Restack reaction plates during incubation so oldest plate is on top. Slide to Multimek™ station.

16. \_\_\_\_\_ 30 minutes after solutions were delivered to compound plate, scan a reaction plate and a filter plate with the barcode scanner at the Multimek™. Place the reaction plate to the left on the Multimek™ deck and the filter plate to the right for transfer.

The Multimek™ procedure will pull up 5 µL air, 100 µL beads from the filter plate, 5 µL air, 20 µL from the reaction plate, and follow with a tip touch on the reaction plate. It will then move back to the filter plate and empty the tips. The tips will then move away from the plates so they may be removed. Tips are to be changed at least every 30 plates. The procedure will be repeated for each compound plate at the appropriate time.

17. \_\_\_\_\_ Wash plates on Flusher™. Begin flushing 30 minutes after the first stack of 15 plates was finished being transferred at the Multimek™

After a filter plate has radioactive solution transferred into it w/Multimek™, it can sit for 1–4 hours before being washed at the Flusher™. The Flusher™ is used to wash/filter the plate to dryness. Wash buffer is 20 mM TEA, pH 7.5, 150 mM NaCl.

The FabD2 program is set for 36 second soak, 1×200 µL, 26 sec.ond soak, 2×150 µL, 21 sec.ond Soak.

After completing the run:

18. \_\_\_\_\_ Clean the cassettes on Multidrops 1 & 2 with water. Spring cassettes loose.

19. \_\_\_\_\_ Rinse Multidrop 3 with water and remove cassette. Place cassette in tip box with a small amount of water to soak.

20. \_\_\_\_\_ Unload Multimek™ tips.

21. \_\_\_\_\_ Wipe all work surfaces with Radiac (plexiglas, multidrops, multimek™ deck, waste container lid exteriors).

22. \_\_\_\_\_ When finished with Flusher™, rinse Flusher™ lines with water to clear out any remaining buffer.

23. \_\_\_\_\_ Shut off vacuum pump. Open red valve to release pressure in Flusher™ waste container. CLOSE VALVE.

24. \_\_\_\_\_ Empty Flusher™ waste.

25. \_\_\_\_\_ Place plates in drying rack and dry completely in the hood.

26. \_\_\_\_\_ Place plates in plate crane racks and load on Trilux to read. Leave stack 1 empty and proceed as with Flusher™ plate crane. Use the Fab2_6 program to read plates.

27. \_\_\_\_\_ Read the plates on the Trilux counter. Download data and barcodes.

Trilux parameters:

sample "normal"

paralux "low bg";

channel "150"

time "30 seconds"

correction "none"

precision "0.20 sig %

Normalized with Chemiluminescence Correction

28. \_\_\_\_\_ Dispose of $^{14}$C-malonyl-CoA waste in the bulk $^{14}$C waste container. Dispose of container in Radioactive Waste.

29. \_\_\_\_\_ Place bins containing radioactive compound plates on a cart and wheel to $^{14}$C waste barrel. Lift bag out of tray and lower into waste barrel. Replace bag.

30. \_\_\_\_\_ Empty Multidrop 1 waste and Flusher™ aspirate waste containers, then add splash of bleach.

31. \_\_\_\_\_ Place remaining wash buffer and bead solution in the refrigerator.

32. \_\_\_\_\_ Save barcode data file and Download barcode data to a disk. (Check that the proper # of barcodes were recorded first and fix if necessary)

33. \_\_\_\_\_ Check compound plates for registration.

34. \_\_\_\_\_ Perform swipe test (on Friday and as needed) on FabD work area. Place results in logbook.

35. \_\_\_\_\_ Analyze the data in HTS Drive and upload QC"d data to BioData Uploader. Test code is FABDHT.

Dispose of filter plates in $^{14}$C solid radioactive waste receptacle.

What is claimed is:

1. A method for identifying an inhibitor of a dual substrate enzyme; wherein a first substrate is a macromolecule that is enzymatically modified, in the presence of the dual substrate enzyme, to accept a radiolabeled portion of a second substrate, said method comprising:

a. adding a capture resin to a buffered mixture of an enzyme, allowing the enzyme to catalyze transfer of the radiolabeled portion of the radiolabeled second substrate to a non-radiolabeled first substrate, in the presence or absence of a test compound;

b. removing unreacted radiolabeled second substrate;

c. adding a scintillant resin to an enzyme-radiolabeled first substrate mixture;

d. measuring the amount of radiolabeled first substrate reacted in the presence of the test compound by scintillation counting, measuring the amount of radiolabeled first substrate reacted in the absence of the test compound by scintillation counting, and comparing the two measurements; and e. wherein when the amount of reacted first substrate is lower in the presence of a test compound than in the absence of the test compound, the test compound is identified as an inhibitor.

2. A method according to claim 1 wherein the first substrate is a peptide or protein.

3. A method according to claim 2 wherein the first substrate is an acyl carrier protein (ACP).

4. A method according to claim 1 wherein the enzyme is a fatty acid biosynthesis enzyme.

5. A method according to claim 1 wherein the enzyme is a phosphate transfer enzyme.

6. A method according to claim 5 wherein the enzyme is a protein kinase or protein phosphatase enzyme.

7. A method according to claim 1 wherein the capture resin is an ionically charged resin.

8. A method according to claim 1 or 7 wherein the scintillant is a scintillation proximity assay resin (SPA) as the scintillant used for measuring the radiolabeled first substrate.

9. A method according to claim 1 wherein unreacted radiolabeled second substrate is removed by filtration.

10. A method according to claim 9 wherein the filtration of radiolabeled second substrate is carried out using an automated filtration and washing apparatus.

* * * * *